(12) United States Patent
Inkpen et al.

(10) Patent No.: US 6,332,875 B2
(45) Date of Patent: Dec. 25, 2001

(54) NEEDLE INJECTION-FACILITATING DEVICE

(76) Inventors: Thomas Randall Inkpen, 37 Kelly Drive, Dartmouth, Nova Scotia (CA), B2W 1N5; Laura Jean Williamson, 21 Saratoga Drive, Dartmouth, Nova Scotia (CA), B2X 3P3

(*) Notice: Subject to any disclaimer, the term of this patent is extended or adjusted under 35 U.S.C. 154(b) by 0 days.

(21) Appl. No.: 09/292,470

(22) Filed: Apr. 15, 1999

(30) Foreign Application Priority Data

Apr. 15, 1998 (CA) ................................................ 2229522

(51) Int. Cl.$^7$ ........................................................ A61M 5/00
(52) U.S. Cl. .......................... 604/181; 604/117; 604/264
(58) Field of Search .................................. 604/181, 136, 604/198, 263, 192, 272, 268, 264, 167, 180, 244, 117; 600/577

(56) References Cited

U.S. PATENT DOCUMENTS

| | | |
|---|---|---|
| 2,845,065 | 7/1958 | Gabriel . |
| 3,612,051 | 10/1971 | Arce . |
| 3,680,559 | 8/1972 | Gorbahn . |
| 4,373,526 | 2/1983 | Kling . |
| 4,601,708 | 7/1986 | Jordan . |
| 4,636,343 | 1/1987 | Shibanai . |
| 4,642,099 * | 2/1987 | Phillips et al. ........................ 604/136 |
| 4,717,383 * | 1/1988 | Phillips et al. ........................ 604/135 |
| 4,769,242 | 9/1988 | Shibanai . |
| 4,898,588 * | 2/1990 | Roberts ................................ 604/187 |
| 5,102,662 | 4/1992 | Gallagher . |
| 5,141,496 | 8/1992 | Dalto et al. . |
| 5,294,445 | 3/1994 | Sleveking et al. . |
| 5,417,662 | 5/1995 | Hjertman et al. . |
| 5,483,973 * | 1/1996 | Benson et al. ........................ 604/187 |
| 5,634,906 | 6/1997 | Haber et al. . |
| 5,833,670 * | 11/1998 | Dillon et al. .......................... 604/263 |
| 5,860,266 | 1/1999 | Martinet et al. . |
| 5,919,168 * | 7/1999 | Wheeler ................................ 604/198 |
| 5,984,898 * | 11/1999 | Garvin .................................. 604/195 |
| 6,004,294 * | 12/1999 | Brimhall et al. ...................... 604/164 |

FOREIGN PATENT DOCUMENTS 536718   2/1957   (CA) .

* cited by examiner

*Primary Examiner*—Richard K. Seidel
*Assistant Examiner*—Kevin C. Sirmons
(74) *Attorney, Agent, or Firm*—Schmeiser, Olsen & Watts

(57) ABSTRACT

A device to aid in the subcutaneous injection of a hypodermic needle has an outer component which is a hollow longitudinal cylindrical sleeve with an inverted frusto-conical base capable of placement on a skin surface, and an inner component which is a hollow cylindrical sleeve of smaller diameter than the outer component and slidably disposed within the outer component. The inner component can hold various size adaptors to customize the device for use with different types or sizes of syringe. Located at the distal end of the inner component is a retaining collar with an aperture sized to receive the hub of a hypodermic needle and through which the needle projects. In a retracted position, the retaining collar rests inside a retaining groove circumscribed within the inner wall of the outer component. The two components slide along a common longitudinal axis in a telescopic arrangement and their movement relative to one another may be controlled by spring means which is compressed when a manual axial force is applied to the syringe prior to insertion of the hypodermic needle. After fluid medication has been delivered at the targeted injection site and the axial force to the syringe is released, the inner component returns to its retracted position with simultaneous extraction of the needle driven by the force of expansion of the spring means.

6 Claims, 5 Drawing Sheets

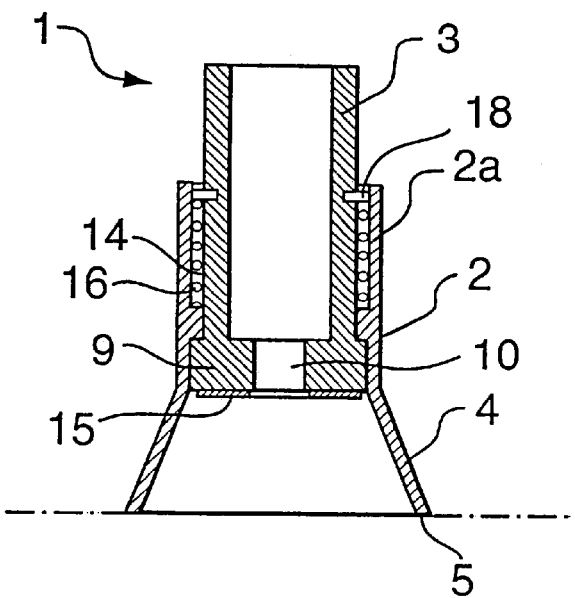
FIG. 2a
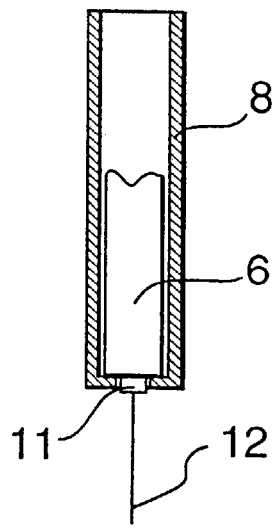
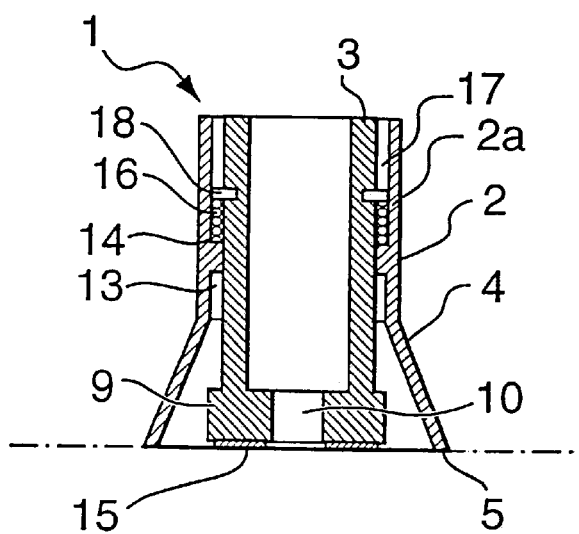
FIG. 2b

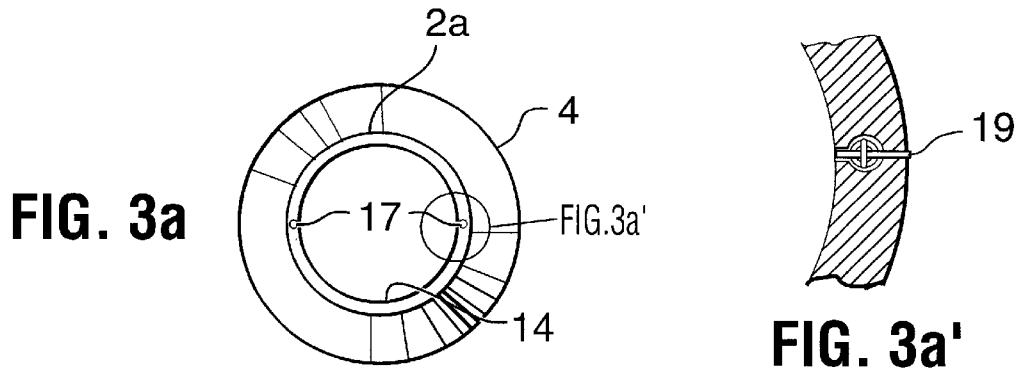
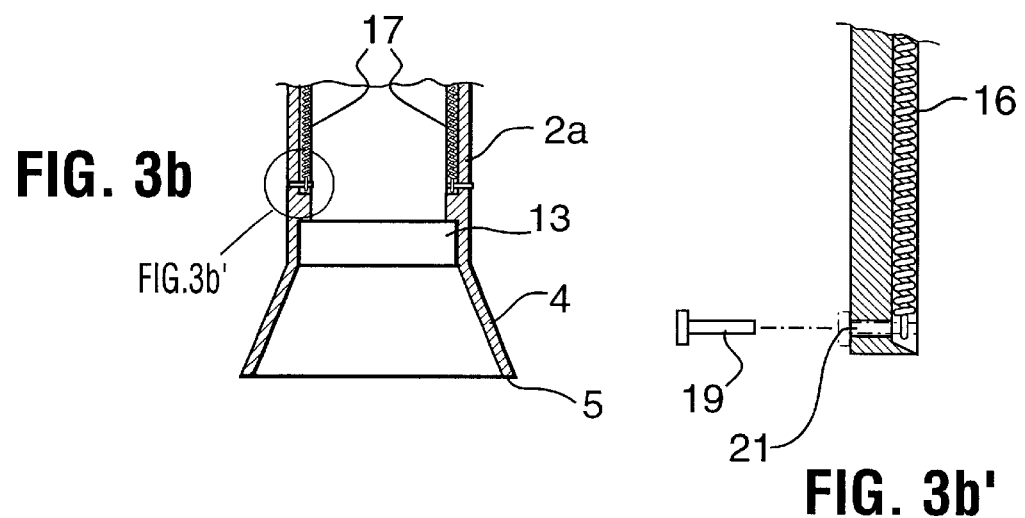
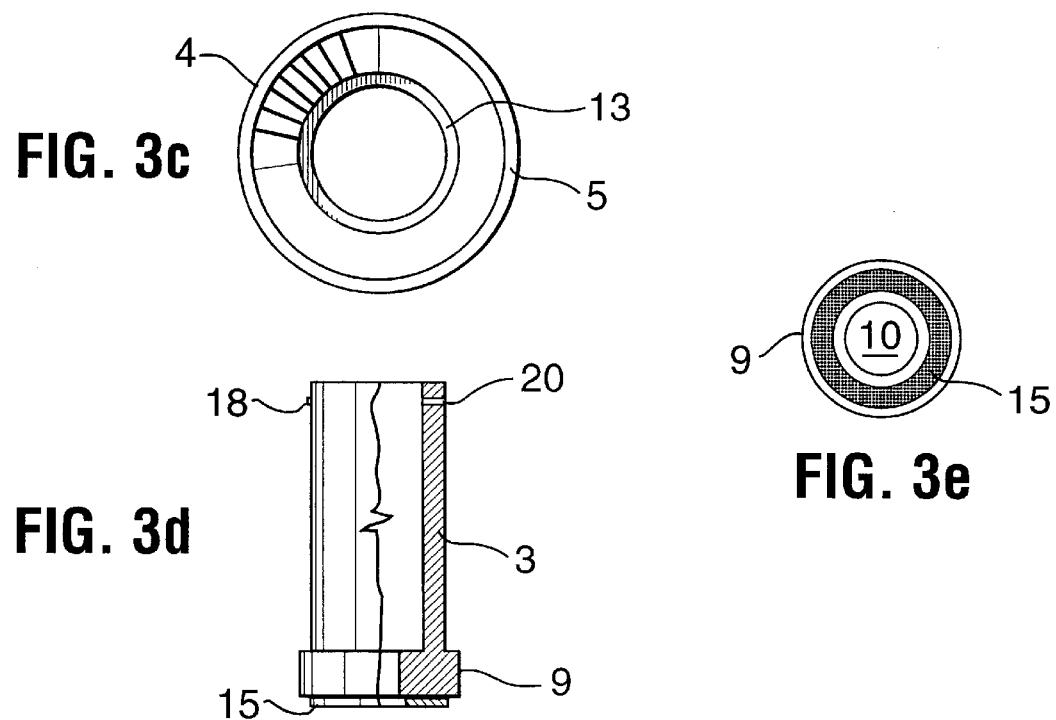

NEEDLE INJECTION-FACILITATING DEVICE

FIELD OF THE INVENTION

The present invention relates to a manually operable needle injection-facilitating device intended for use as an aid in the injection of fluid medication by means of a hypodermic syringe or medication pen. The invention is particularly useful to patients who are frequently required to self-administer medication such as insulin in the case of diabetes.

The major difficulty that exists in the self-handling of a hypodermic syringe or medication pen by a person other than a trained professional is the accurate insertion and penetration of the needle into the skin of the patient. This problem is particularly compounded for individuals who are visually impaired, have an aversion to needles and injections, or lack fine motor control in attempting to administer their own medication.

DESCRIPTION OF BACKGROUND ART

Various injector assist devices for facilitating hypodermic injections for in-home use, such as for insulin injections, are known for operation with conventional hypodermic syringes while simultaneously controlling the depth of penetration of the hypodermic needle. However, for an individual with impaired vision or manual dexterity, these injector assist devices have a number of disadvantages that make them inconvenient and less desirable to use. One disadvantage associated with some present injector assist devices is that, by virtue of the number of components from which the devices are comprised, they are complicated with respect to assembly of the device. For example, in the case of U.S. Pat. No. 5,634,906 of Haber et al., several components of the apparatus are adapted with various peripheral retaining grooves and ridges so that they may interface precisely in combination with each component of a dose metering syringe, i.e. the medication housing, medication cartridge, needle hub and barrel. As such, considerable coordination is required to ensure that each component of the device is properly interfaced in combination with each component of the syringe so that it may function properly. Another disadvantage found among other injector assist devices is that they have components sized to accommodate only a limited number of commercial syringes and therefore, are not compatible with a medication pen. Examples of these devices are disclosed in U.S. Pat. No. 4,601,708 of Jordan and Canadian Patent No. 536,718 of Transue. On the other hand, some prior art injector devices are more simplistic in design, comprising essentially one tubular component adapted to fit over the barrel of a syringe. Such devices, described, for instance, in U.S. Pat. No. 5,417,662 of Hjertman et al. and U.S. Pat. No. 4,373,526 of Kling, have a number of angled surfaces within the interior wall of a tube, which are designed to inter-fit and inter-engage with annular projections of a conventional syringe barrel. However, the interlocking arrangement between the injector assist device and the syringe makes the device more difficult to manipulate in terms of its attachment to and/or removal from a syringe, especially for a person with poor manual dexterity.

SUMMARY OF INVENTION

Accordingly, an object of the invention is to provide an injector assist device comprised of a minimal number of component parts, which can be quickly and easily incorporated with either a conventional hypodermic syringe or a medication pen, is easy to handle and manipulate, and can reliably and safely facilitate administration of a medicament dosage, particularly by an individual who is visually impaired or lacks fine motor control.

Another object of the invention is to provide an improved needle injection-facilitating device which by function and structural design can accommodate a conventional hypodermic syringe or medication pen and which greatly simplifies and safely facilitates the self-injection procedure for in-home use application.

According to the invention there is provided a needle injection-facilitating device to aid in the positioning, guiding and stabilization of a hypodermic syringe or medication pen for subcutaneous injection, comprising in combination:

(a) an outer hollow cylindrical sleeve opening into an inverted frusto-conical base capable, in use, of shielding a hypodermic needle from view prior to and during an injection;

(b) an inner hollow cylindrical sleeve disposed within the outer sleeve and capable of sliding movement therein, between a retracted position and an operating position, said inner sleeve being adapted to receive a syringe or medication pen;

(c) biasing means disposed between the inner sleeve and the outer sleeve which upwardly biases the inner sleeve to said retracted position in which a hypodermic needle received within said inner sleeve is shielded from view by the base of said outer portion; and (d) whereby upon placement of the conical base of said outer sleeve in contact with an injection site followed by application of a downward axial force to a syringe or medication pen received in said inner sleeve advances the inner sleeve from the retracted position to the operating position to effect administration of an injection; and subsequent removal of said downward force permits movement of said inner sleeve back to the retracted position and extraction of the hypodermic needle of said syringe or medication pen from the injection site.

Thus, the invention affords a needle injection-facilitating device designed for use with a hypodermic syringe or medication pen. The device comprises an outer hollow longitudinal cylindrical sleeve of larger diameter with an inverted frusto-conical base that allows a 90° angle of insertion of a hypodermic needle subcutaneously into a patient. In a second embodiment of the device, the frusto-conical base is beveled to allow a 45° angle of insertion. By beveling the base of the outer sleeve in this way, a preferred angle of insertion at the targeted injection site can be achieved for a particular medical application while reducing the possibility of a bent syringe needle. The frusto-conical base also assists in guiding and stabilizing the movement of the hypodermic syringe, or medication pen, at a particular location by an individual who is visually impaired or lacks fine motor control. Furthermore, because the base of the outer sleeve shields the hypodermic needle from view prior to and during injection, the psychological barrier of needle insertion will be alleviated for the user who may experience anxiety at the sight of an exposed needle.

An inner hollow cylindrical sleeve of smaller diameter is slidably disposed within the outer sleeve and can hold various size adaptors to customize the device for use with a given type or size of syringe. Located at the distal end of the inner sleeve is a retaining collar with an aperture sized to receive the hub of a hypodermic needle and through which the needle projects. In a retracted position, the retaining collar rests inside a retaining groove circumscribed within the inner wall of the outer sleeve. A velcro patch may be attached on the outside face of the distal end of the inner sleeve and has a diameter and inner hole sized to match the dimensions of the retaining collar and its aperture, respectively.

The two sleeves slide along a common longitudinal axis in a telescopic arrangement and their movement relative to one another is controlled by biasing means, such as of spring means, which advantageously comprises springs disposed inside a pair or plurality of grooves set within the inner wall of the outer sleeve. The springs are compressed when an axial force is applied to the syringe prior to and during insertion of the hypodermic needle. In another embodiment of the injection needle-facilitating device, a single helical coil spring encircles the upper portion of the inner sleeve and seats on the peripheral edge at the extreme proximal end of the outer sleeve. An adjustable retaining ring located at the proximal end of the inner sleeve secures the spring to the device. Adjustment of the retaining ring will determine the tension of the spring and to a lesser degree, the extent of needle projection beyond the inner sleeve.

The depth of penetration of the hypodermic needle is determined by the exterior face of the inner sleeve coming in contact with the skin surface of the user. This automatically accommodates non-flat, e.g. concave or convex body surfaces, where the point of injection is non-planar with the periphery of the frusto-conical base. After fluid medication has been delivered at the targeted injection site, the needle is extracted by the force of expansion of the spring following release of the axial force to the syringe.

Another embodiment of the device simply comprises a fixed outer component which is a hollow longitudinal cylindrical sleeve with an inverted frusto-conical base that allows a 90° placement on the skin surface. The inner dimensions of the fixed sleeve enable it to be coupled to a medication pen, however, the sleeve can be easily adapted for use with commercial type hypodermic syringes by insertion of various size adaptors. Located at the distal end of the fixed sleeve is an aperture sized to receive the hub of a hypodermic needle and through which the needle projects. In the case of the operation of the fixed sleeve, it is initially positioned at the preferred injection site of the user utilizing the inverted frusto-conical base as a guide. In other words, for this particular embodiment of the injection needle-facilitating device, the fixed sleeve is not assembled with the barrel of a syringe prior to its placement on the surface of the skin. Once the user has chosen a preferred injection site by orientation of the fixed sleeve, the syringe is then inserted through the sleeve during the injection procedure. In this way, the frusto-conical base of the fixed sleeve serves to guide, position and stabilize the movement of the syringe by a visually or manually impaired individual while ensuring the proper angle and depth of entry of the needle, thereby reducing the possibility of a bent syringe needle.

In the following description, the invention will be explained in detail with the aid of the accompanying drawings which illustrate preferred embodiments of the present invention:

BRIEF DESCRIPTION OF THE DRAWINGS

FIGS. 2a and 2b are cross-sectional views of a needle injection-facilitating device of FIG. 1 in a normal retracted position and a compressed position, respectively, without attachment to a hypodermic syringe or medication pen;

FIGS. 3a to 3e show plan and cross-sectional views of components which comprise the needle injection-facilitating device of FIG. 2;

DETAILED DESCRIPTION

Figure 1A:
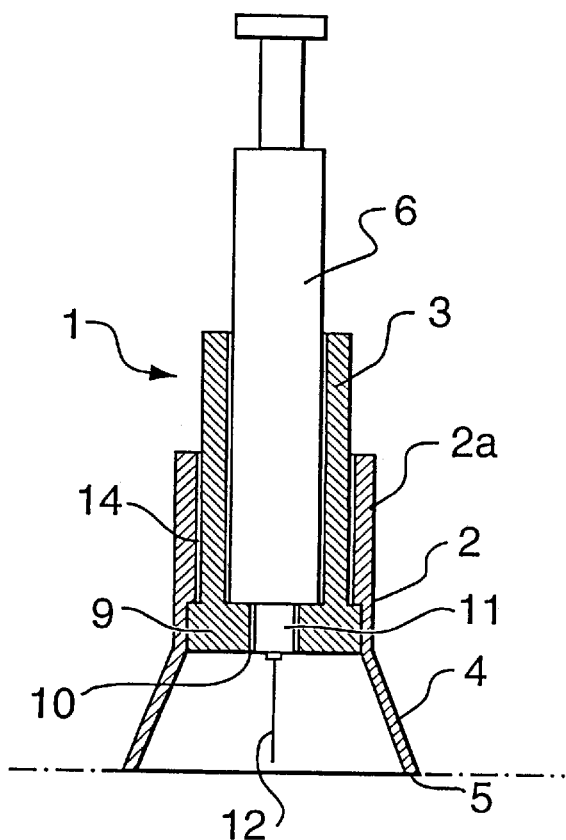
FIGS. 1a and 1b are cross-sectional views of a needle injection-facilitating device in combination with a hypodermic syringe in a retracted and an operating position, respectively, following placement at a targeted injection site.

As illustrated in FIGS. 1 to 3, a first embodiment of a needle injection-facilitating device 1 comprises an outer component 2 which is a hollow, longitudinal cylindrical sleeve portion 2a surmounting an inverted frusto-conical base 4 the periphery 5 of which is normal to the surface of the skin upon placement of the needle injection-facilitating device 1 thereon. An inner component 3 is a hollow cylindrical sleeve dimensioned to receive the distal end of the barrel of a hypodermic syringe 6, or medication pen 7, and to be slidably disposed within the outer component 2. The inner component 3 can also hold various size adaptors 8 to customize the device for use with a particular type or size of syringe. Located at the distal end of the inner sleeve 3 is a retaining collar 9 with an aperture 10 sized to receive the hub 11 of a hypodermic syringe 6 and through which a needle 12 of such syringe projects. In a retracted position, the retaining collar 9 rests inside a retaining groove 13 circumscribed within the inner wall 14 of the outer sleeve 2. A velcro® (hook and loop fastener) patch 15, fixed on the outside face of the distal end of the inner sleeve 3, has a diameter and inner hole sized to match the dimensions of the retaining collar 9 and its aperture 10, respectively. The two components 2 and 3 are coaxially aligned relative to one another and the inner component 3 slides along a common longitudinal axis in a telescopic arrangement. Their movement is controlled by means of a pair of springs 16 which are compressed when an axial force is applied to the syringe 6 prior to and during insertion of the hypodermic needle 12. A pair of longitudinal grooves 17, circumscribed at diametrically opposed locations within the inner wall 14 of the outer sleeve 2, house the pair of springs 16. Each spring 16 is secured by means of a pair of pins 18 and 19. The upper portion of each spring 16 is held in place by a pin 18 which is inserted through pin-holes 20 located at the proximal end of the inner sleeve 3 and within the pair of grooves 17. The lower portion of each spring 16 is held in place by a pin 19 inserted through pin-holes 21 located within the wall of the outer sleeve 2 located at its distal end. When a downward axial force is applied, the pair of pins 18 slide within the grooves 17 formed in the inner wall 14 of the outer sleeve 2 thereby compressing the springs 16. After the fluid medication has been delivered at the targeted injection site, release of the axial force on the syringe 6 permits the expansive force of the springs 16 to drive the inner sleeve 3 back to its original retracted position while, simultaneously extracting the hypodermic needle 12 from the injection site.

Figure 1B:
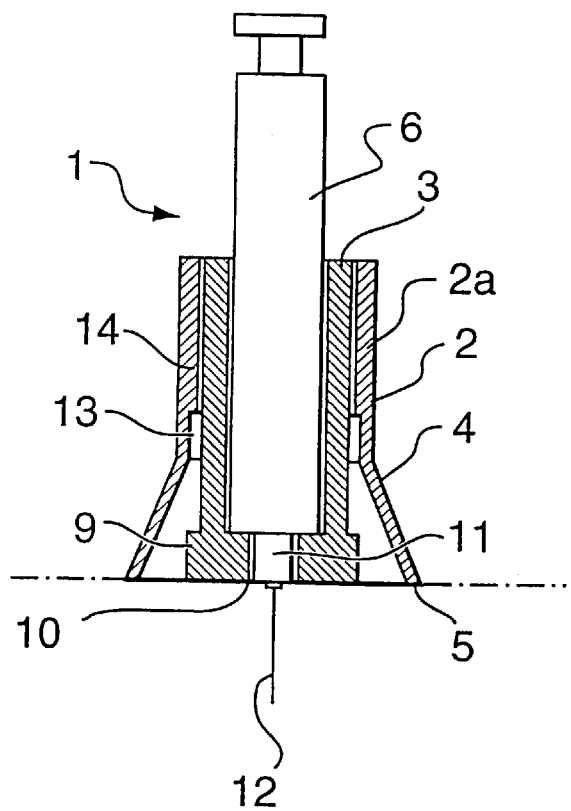

In the rest condition of FIG. 1a, the inner sleeve 3 which encloses the barrel of the syringe 6 is biased in a retracted position relative to the outer sleeve 2 such that the retaining collar 9 of the inner sleeve 3 sits inside the retaining groove 13 of the outer sleeve 2. In this position, the hypodermic needle 12 is shielded from view when the needle injection-facilitating device 1 is placed on the skin surface at the targeted injection site. The pair of springs 16 housed in the grooves 17 of the inner wall 14 of the outer sleeve 2 are in a relaxed conformation. Prior to coupling the needle injection-facilitating device 1 with the syringe 6, an alcohol swab may be attached to the velcro patch 15 located at the distal face of the inner sleeve 3. After the needle injection-facilitating device 1 is assembled with the hypodermic syringe 6, or medication pen 7, it is placed on the skin surface at the desired injection site. The large surface area circumscribed by the periphery 5 of the inverted frusto-conical base 4 helps to stabilize the orientation of the syringe 6 so that the direction of the needle 12 is maintained in a position perpendicular to the surface of the skin. When a downward axial force is applied to the main barrel of the syringe 6, as illustrated in FIG. 1b, the inner sleeve 3 is advanced distally resulting in compression of the springs 16. As the hypodermic needle 12 begins to penetrate the skin, the movement of the inner sleeve 3 continues until the exterior face of the retaining collar 9 comes in contact with the surface of the skin, thereby controlling the depth of penetration of the needle 12. When injection of the fluid medication has been administered in the conventional manner, subsequent release of the axial force permits the springs 16 to expand to their relaxed conformation. The force of expansion of the springs 16 propels the inner sleeve 3 back to its original retracted state, while simultaneously extracting the hypodermic needle 12 into a shielded position within the frusto-conical base 4 of the device 1.

Figure 4A:
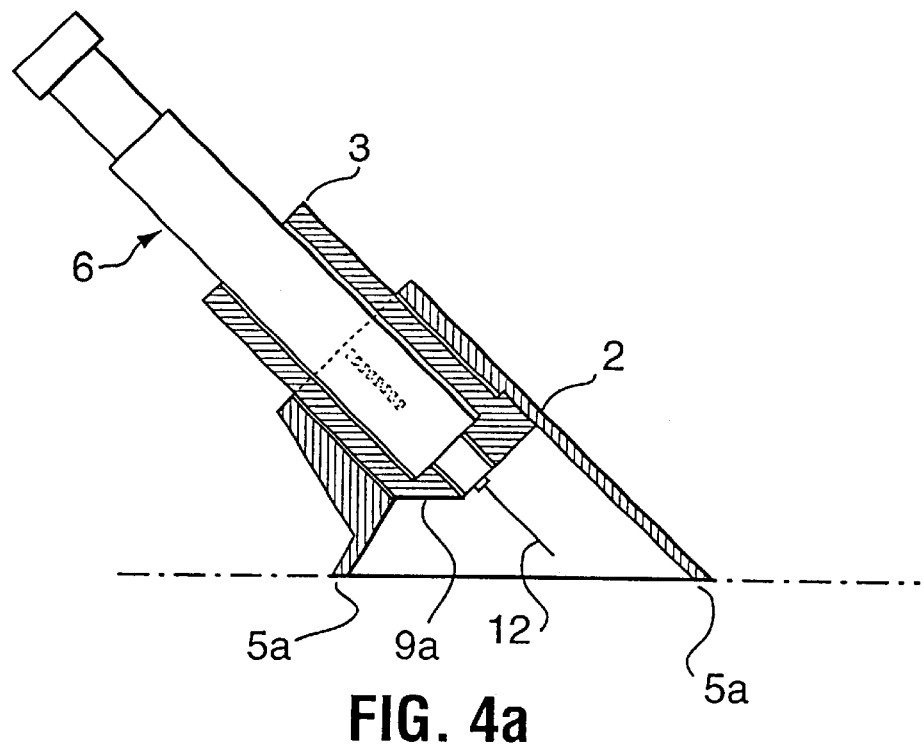
FIGS. 4a and 4b show cross-sectional views of a second embodiment of a needle injection-facilitating device in combination with a hypodermic syringe in a retracted and an operating position, respectively, following placement at a targeted injection site.
Figure 4B:
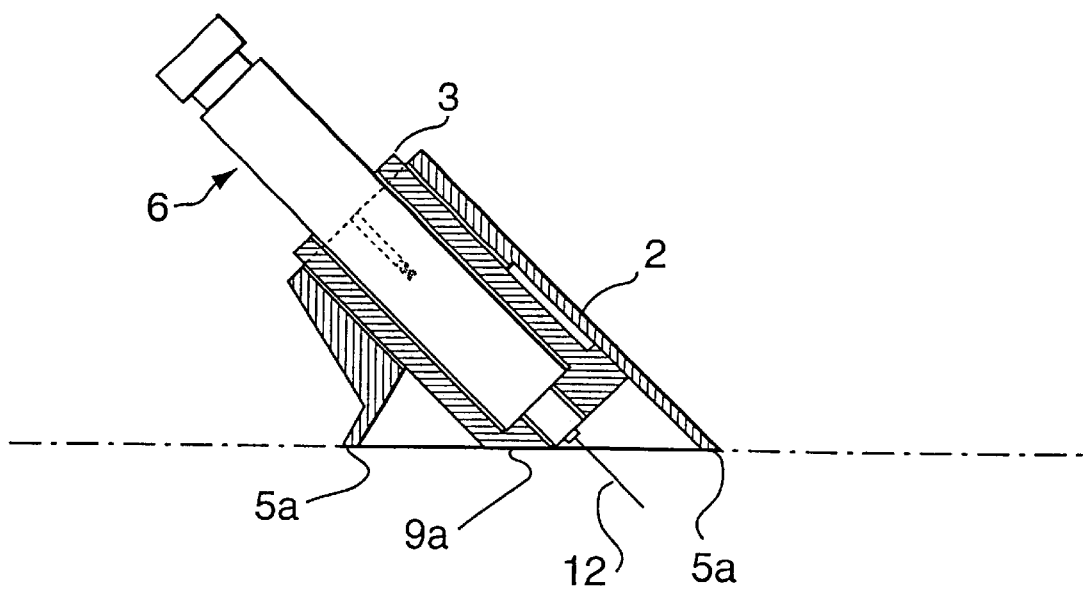

A second embodiment of the injection needle-facilitating device 1 is illustrated in FIGS. 4a and 4b in which the periphery 5a of the inverted frusto-conical base is beveled to allow a 45° insertion of the hypodermic needle 12 relative to placement of the device on the skin surface. In this embodiment the end face 9a of the inner sleeve 3 is also offset or beveled to permit flat contact thereof with a skin surface. FIGS. 4a and 4b provide an illustration of the device 1 in both a resting and injection position, respectively. The method of operation of the device 1 in this particular embodiment is essentially the same as that described above for FIGS. 1a and 1b.

Figure 5:
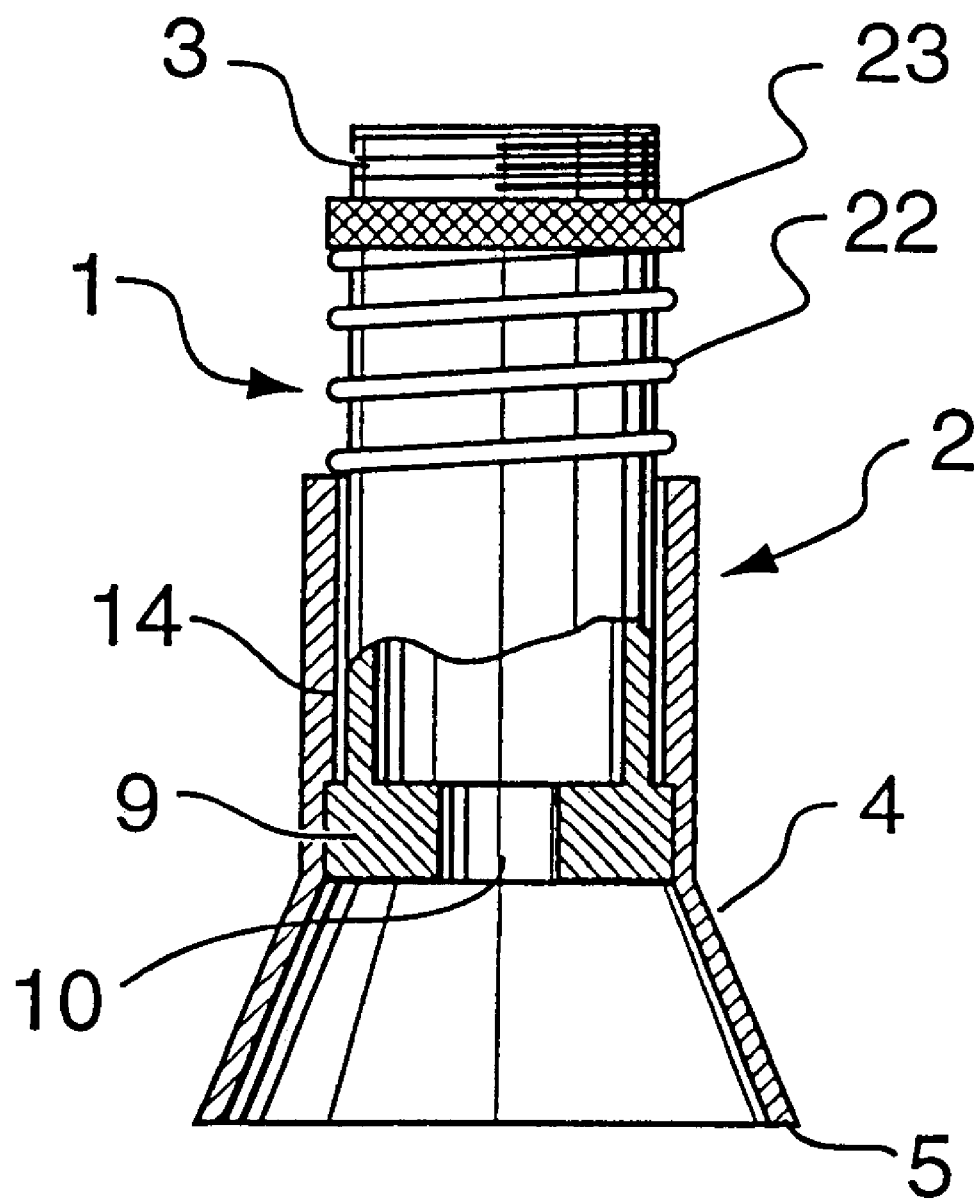
FIG. 5 is a side view, party in cross-section, of a needle injection-facilitating device according to a third embodiment of this invention.

The injection needle-facilitating device 1 of the embodiment shown in FIG. 5 incorporates a single helical coil spring 22 which encircles the upper portion of the inner sleeve 3 while resting on the peripheral edge at the extreme proximal end of the outer sleeve 2. An adjustable retaining ring 23, located towards the proximal end of the inner sleeve 3, secures the helical spring 22 to the device 1. The retaining ring 23 has a set of screw threads to match those extending around the exterior of the inner sleeve 3 at the proximal end thereof. Adjustment of the retaining ring 23 will vary the tension of the spring 22 and, to a lesser degree, the extent of needle 12 projection beyond the distal end of the inner sleeve 3. As FIG. 5 illustrates, the helical spring 22 is in a relaxed conformation when the device 1 is in a resting condition. As such, the inner sleeve 3 is biased in retracted a position relative to the outer sleeve 2. In this position, the hypodermic needle 12 is shielded from view.

FIGS. 6a to 6c illustrate another embodiment of the injection needle-facilitating device 1 which comprises a fixed outer component which is a hollow longitudinal cylindrical sleeve 24a opening into an inverted frusto-conical base 25 that allows a 90° placement on the skin surface. The frusto-conical base 25 serves to guide, position and stabilize the movement of a syringe by a visually or manually impaired individual while ensuring a proper angle of insertion and reducing the possibility of a bent syringe needle. The inner dimensions of the fixed sleeve 24 enable it to be coupled to a medication pen 7. However, the sleeve 24 can be easily adpated for use with other commercial-type hypodermic syringes by attachment with various size adaptors. Located at the distal end of the fixed sleeve 24 is an aperture 26 sized to receive the hub 11 of a hypodermic syringe 6 and through which the needle 12 projects. Any of the above injection needle-facilitating devices may be fabricated from either metal or heat-resistant plastic.

Any of the above injection needle-facilitating devices may be fabricated from either metal or heat-resistant plastic.

We claim:

1. A needle injection-facilitating device comprising:
   (a) an outer hollow sleeve opening into a flared base;
   (b) an inner hollow sleeve having an interior surface configured to receive a syringe or medication pen, said inner sleeve having a retaining collar at its distal end with an aperture sized to receive a hub of a hypodermic needle and through which the needle projects, wherein said inner sleeve is capable of sliding movement inside said outer sleeve, between a retracted position and an operating position; and
   (c) biasing means disposed between the inner sleeve and the outer sleeve which upwardly biases the inner sleeve to said retracted position in which a hypodermic needle received within said inner sleeve is shielded from view by the base of said outer sleeve;
   whereby placement of the flared base of said outer sleeve in contact with an injection site followed by manual application of a downward axial force to a syringe or medication pen received in said inner sleeve advances the inner sleeve from the retracted position to the operating position against the bias of said biasing means to effect administration of an injection; and subsequent removal of said downward force permits movement of said inner sleeve under the influence of said biasing means back to the retracted position and concomitant extraction of the hypodermic needle of said syringe or medication pen from the injection site.

2. A needle injection-facilitating device according to claim 1, in which the biasing means comprises a plurality of springs disposed within grooves formed longitudinally in the inner wall of the outer sleeve.

3. A needle injection-facilitating device according to claim 1, in which the biasing means comprises a helical coil spring surrounding an upper portion of the inner sleeve and extending between the top of the outer sleeve and an adjustable retaining ring located near the top end of the inner sleeve.

4. A needle injection-facilitating device according to claim 1 in which the flared base is beveled to accommodate an acute angle of insertion of a needle.

5. A needle injection-facilitating device according to claim 1 and further comprising a cylindrical adaptor for insertion in the inner sleeve, to accommodate a particular size of medication pen or hypodermic syringe.

6. A needle injection-facilitating device according to claim 1 in which a hook-and-loop fastener patch is fixed to the lower face of the distal end of the inner sleeve, to facilitate the adhesion of a sterilizing swab.

* * * * *